United States Patent [19]

Thomas

[11] Patent Number: 4,966,594

[45] Date of Patent: Oct. 30, 1990

[54] APPARATUS FOR PREVENTING THE SPREADING OF ACQUIRED IMMUNE DEFICIENCY SYNDROME (AIDS)

[76] Inventor: Herman A. Thomas, 2221 Orange Blossom La., Bradenton, Fla. 33507

[21] Appl. No.: 91,455

[22] Filed: Aug. 31, 1987

Related U.S. Application Data

[63] Continuation-in-part of Ser. No. 72,677, Jul. 18, 1987, abandoned.

[51] Int. Cl.[5] ............................................. A61F 5/44
[52] U.S. Cl. .................................... 604/349; 604/353
[58] Field of Search .............................. 604/349–353, 604/346; 224/226

[56] References Cited

U.S. PATENT DOCUMENTS

| | | | |
|---|---|---|---|
| 3,749,096 | 7/1973 | Donaldson | 604/353 |
| 4,073,295 | 2/1978 | Laufbahn | 604/353 |
| 4,664,104 | 5/1987 | Jaicks | 604/353 |
| 4,685,913 | 8/1987 | Austin | 604/353 |

FOREIGN PATENT DOCUMENTS

| | | | |
|---|---|---|---|
| 657004 | 2/1963 | Canada | 604/349 |
| 13560 | 1/1897 | Switzerland | 604/349 |

Primary Examiner—Randall L. Green
Assistant Examiner—Randy Shay
Attorney, Agent, or Firm—Gifford, Groh, Sprinkle, Patmore and Anderson

[57] ABSTRACT

A device to prevent the spread of Acquired Immune Deficiency Syndrome virus or AIDS comprises an elastic belt worn around the hips or mid-body portion of a male person. From the belt depends a tab and means for securing thereto a condom which means is removable after sexual intercourse.

In an improved device according to the invention, a grip is carried by the belt and is connectable to the condom.

4 Claims, 2 Drawing Sheets

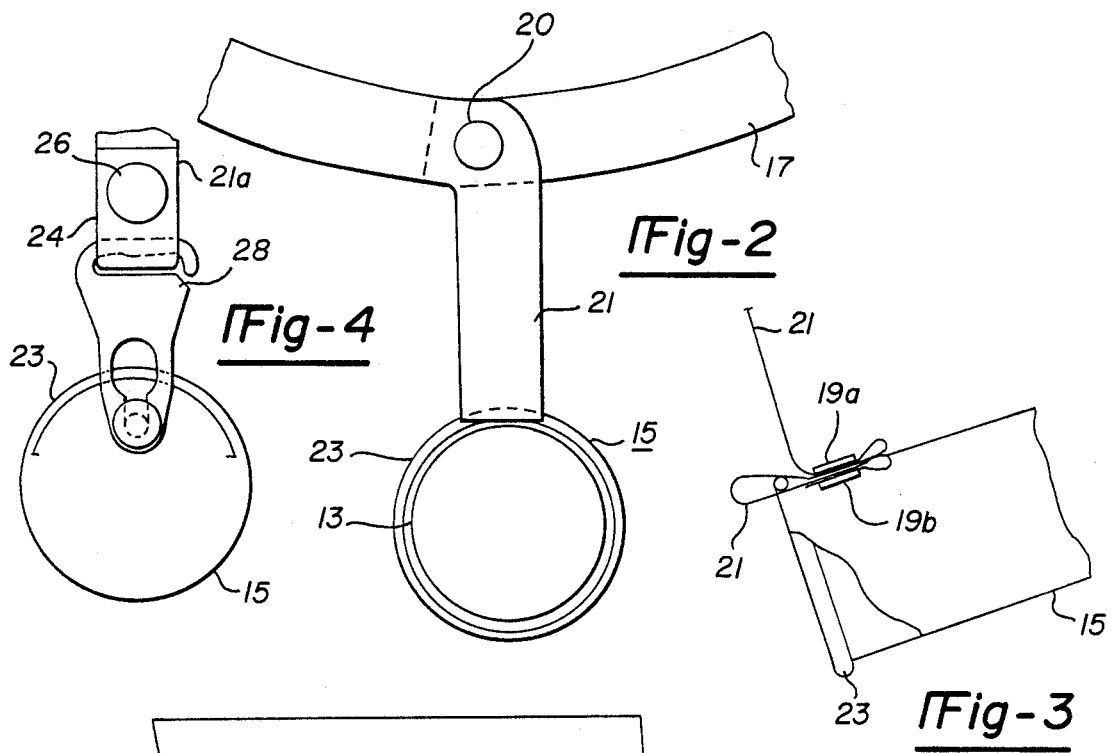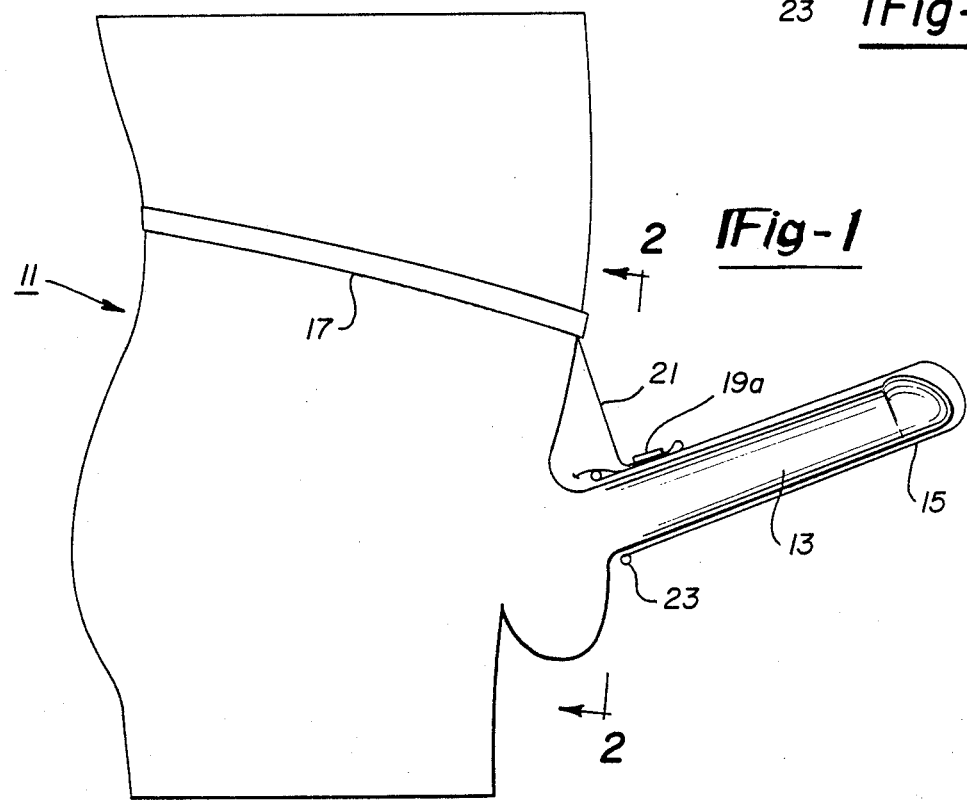

APPARATUS FOR PREVENTING THE SPREADING OF ACQUIRED IMMUNE DEFICIENCY SYNDROME (AIDS)

CROSS REFERENCE TO RELATED APPLICATION

This application is a continuation-in-part of application Ser. No. 072,677 filed July 18, 1987 now abandoned.

BACKGROUND OF THE INVENTION

The present invention is concerned with Public Health and Welfare and, as such, is an important contribution to the prevention of the spreading of Acquired Immune Deficiency Syndrome, commonly called AIDS virus.

AIDS, at the present time, is an alarming Public Health problem and there is no present cure for this terrible disease. In its most severe form, AIDS is a complete collapse of a person's natural immune system that leaves the person without resistance to infections.

There is no evidence at present that AIDS is spread casually. Sexual contact, blood contact, and the transmission from an infected mother to a child account for almost all of the presently known causes of AIDS patients.

Any individual with multiple sexual partners, or any partner that may have had multiple sexual partners is a risk for AIDS.

People with AIDS are largely members of certain groups know as "high risk" groups. Such persons are mainly male homosexuals or bisexual males, and the disease is more frequent among men who have a large number of sexual partners.

The AIDS virus is transmitted through body fluids, specifically semen during sexual intercourse and blood through sharing hypodermic needles and syringes.

Because the AIDS virus is easily transmitted by semen during sexual intercourse, it is proposed to apply to the erected phallus a prophylactic device, such as a condom, whereby semen when it is ejaculated is caught in the device. But, in some instances, the condom becomes separated from the phallus and the semen is not caught in the condom. Wherefore, the effect is to transmit the AIDS virus unintentionally.

The present invention comprises a method and a device that is useful to prevent the separation of the condom from the phallus during sexual intercourse.

SUMMARY OF THE INVENTION

The present invention comprises an elastic belt worn by a male person, and from the belt, in one embodiment of the invention, depends a strap or tab that has means for attachment to a condom, thereby preventing the condom from becoming separated from the phallus during and after sexual intercourse.

In another embodiment of the invention, a grip is carried on the belt and the grip connects to and prevents the condom from becoming separated from the phallus.

It is a primary object of the present invention to provide apparatus that prevents a condom from becoming separated from an erected phallus during and after sexual intercourse.

The many other objects and features as well as advantages of the present invention will become apparent to those skilled in the art from the following description of the best mode contemplated for practicing the invention when it is read in conjunction with the accompanying drawings wherein like numerals refer to like or equivalent parts.

BRIEF DESCRIPTION OF THE DRAWINGS

In the drawing:

FIG. 1 is a side elevation view of a male person's mid-body showing a preferred embodiment of the invention worn by such male person;

FIG. 2 is a front partial sectional view along line II—II of FIG. 1;

FIG. 3 is a side view showing a portion of a condom connected to the AIDS safety belt of the present invention;

FIG. 4 is a front view of another means for securing the condom to the belt of the present invention;

DETAILED DESCRIPTION

Figure 6:
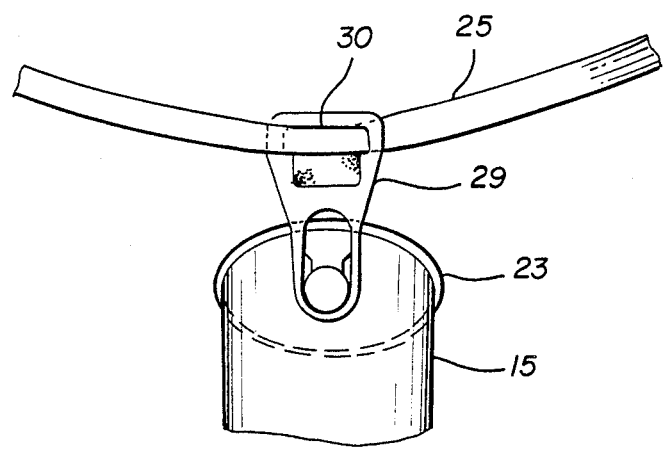
FIG. 6 is a front view of the improved embodiment of the invention, a grip, connected to a condom.

Referring to FIG. 1, a profile view of the hips and midbody body portion of a male person 11 shows an erect phallus 13 on which is a conventional condom 15. Surrounding the hips and mid-body portion of the male person 11 is an elastic, web-type belt 17 having one end fastened by a rivet 20 to the other end portion so as to form a dependent tab 21 having at its free end a conventional snap fastener with one part 19a separated from the other part 19b.

FIG. 2 illustrates a front partial sectional view along line II—II of FIG. 1 and shows the erect phallus 13 on which is the conventional condom 15 having the ring portion 23 located thereon. The ring portion 23 interconnects the dependent tab 21 as is described with respect to FIG. 3 below. As described above with respect to FIG. 1, the elastic belt 17 has one end fastened by the rivet 20 to its other end so as to form the dependent tab 21.

FIG. 3 illustrates in an enlarged view a portion of the device of FIG. 1 and shows how the tab 21 is looped. The ring portion 23 of the condom 15 is placed in the loop and the top portion of the conventional fastener 19a, 19b are mated to secure the condom 15 in place.

Referring to FIG. 4, in a modification of the device of the present invention, a tab 21a depending from the elastic belt 17 has at its free end a loop secured preferably by a rivet 26. In the loop 24 is a conventional hose or stocking clip 28 that engages the ring portion 23 of the condom 15.

Figure 5:
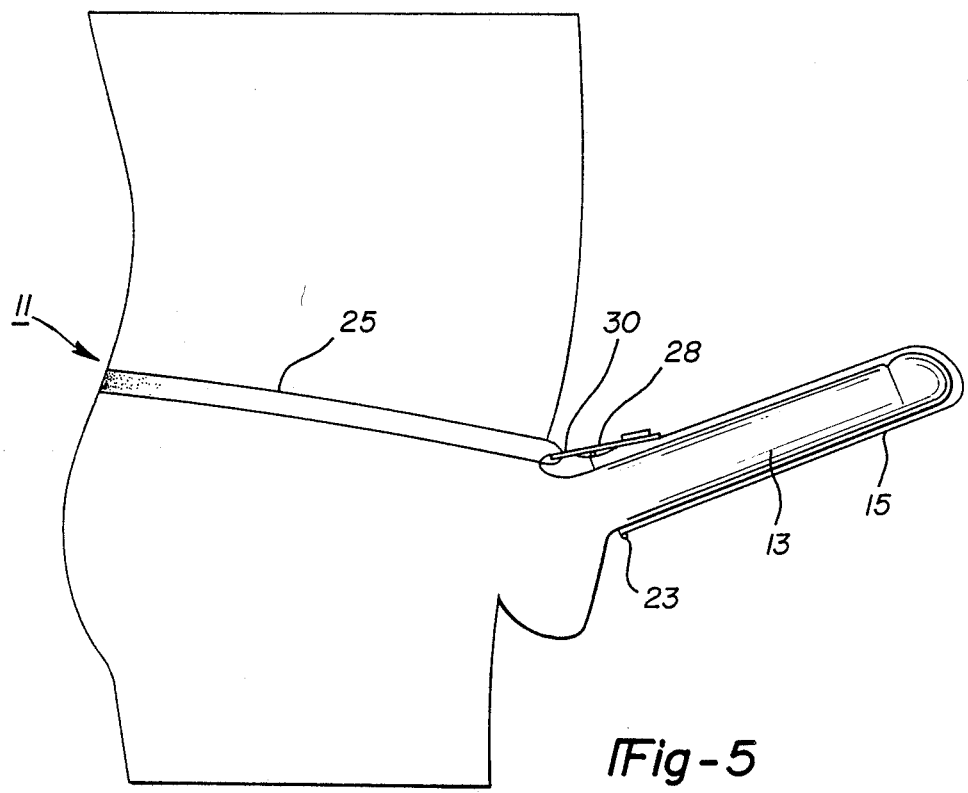
FIG. 5 is a side elevational view of a male person's midbody showing an improved embodiment of the present invention as worn by such person.

FIGS. 5 and 6 illustrate an improved form of the present invention that comprises a narrow width of elastic belt 25 that is worn around the mid-body, close to the hips, of a male person. A conventional grip 29, having a loop 30 at the top is slidable on the belt 25 and is connected to the ring portion 23 of the condom 15.

The method of using the device of the present invention is first to surround the phallus with a condom; second, to put the belt around the mid-body of the male person; third to attach the tab to the ring portion of the condom.

The method of using the improved form of the invention, as shown in FIGS. 5 and 6, is to place the belt 25 around the mid-body near the hips of the male person and secure the grip 28 to the ring portion of the condom 15.

From the foregoing description of a preferred embodiment of the invention, and from the improvement therein, those who are skilled in the art will recognize its many features and advantages. Among the many features and advantages the following are significant:

That the condom is secured to the AIDS safety belt during sexual intercourse and after ejaculation, the condom will not slip off the phallus when it is withdrawn;

That the body of the male person is not exposed to fluids that may carry AIDS virus that could infect such person;

That the present invention is relatively inexpensive and is useful in promoting Public Health and Wellfare;

That the belt of the invention is made of elastic material that hugs the hip portion of the male person tightly thereby preventing the belt from slipping of the hip portion of the wearer;

That the belt is elastic and easily fitted to the hip portion of a male person of any size; and That the condom can be easily and quickly attached to the belt and detached therefrom as easily;

Although the present invention has been described with a certain degree of particularity, it is understood that other modifications may be made therein without departing from the scope of the invention as defined by the following claims.

What is claimed is:

1. A device for preventing the spread of acquired Immune Deficiency Syndrome, commonly called AIDS, virus comprising:
    a belt surrounding the mid-body and hip portion of a male person, said belt having a front portion and a back portion;
    a single tab depending from said front portion of said belt;
    a condom;
    means for removably securing said condom to said tab;
    said condom conventionally having a ring portion;
    said tab being of sufficient length so that a free end of said tab is adjacent the ring portion of the condom when worn, said tab having a loop at its free end;
    wherein said removable securing means comprises a conventional stocking clip having a hook at one end and an opening at its other end, said opening having an enlarged area portion and a reduced area portion;
    said clip hook being removably attachable to said tab by inserting said hook through said tab loop.

2. The device of claim 1 wherein said stocking clip of said removable securing means further comprises means for fastening, said means being positioned through a portion of said condom adjacent the ring, into the enlarged area opening of the clop and then into the reduced area opening of said clip.

3. A device for preventing the spread of Acquired Immune Deficiency Syndrome, commonly called AIDS, virus comprising:
    a belt surrounding the mid-body and hip portion of a male person, said belt having a front portion and a back portion;
    a single tab depending from said front portion of said belt;
    a condom,
    means for removably securing said condom to said tab;
    said condom conventionally having a ring portion;
    said tab being of sufficient length so that a free end of said tab is adjacent the ring portion of the condom when worn, said tab having a loop at its free end;
    wherein said removable securing means comprises a conventional stocking clop having a hook at one end and an opening at its other end, said opening having an enlarged area portion and a reduced area portion;
    said clip hook being removably attachable to said tab by inserting said hook through said tab loop;
    a conventional stocking button being positioned through a portion of said condom adjacent the ring, into the enlarged area opening of the clop and then into the reduced area opening of said clip.

4. The device of claim 3 wherein said belt has a first end and a second end, said first end and said second end being fixedly interconnected by a rivet, said rivet being so positioned as to form said tab depending form said rivet, said belt being composed of an elastic material.

* * * * *